United States Patent [19]

Hinzmann et al.

[11] Patent Number: 5,004,467

[45] Date of Patent: Apr. 2, 1991

[54] TAMPON

[75] Inventors: Alfred Hinzmann, Weems; Timour T. Shu; Wojciech S. Drewnowski, both of Richmond; Peter M. Preisner, Quinton, all of Va.

[73] Assignee: Hauni Richmond, Inc., Richmond, Va.

[21] Appl. No.: 416,997

[22] Filed: Oct. 4, 1989

[51] Int. Cl.$^5$ ............................................. A61F 13/15
[52] U.S. Cl. ..................................... 604/904; 604/330
[58] Field of Search ............... 604/358, 378, 327, 328, 604/330, 904, 385.1

[56] References Cited

U.S. PATENT DOCUMENTS

| | | | |
|---|---|---|---|
| 710,670 | 6/1954 | Amandi | 604/904 |
| 2,188,923 | 2/1940 | Robinson | 604/904 |

Primary Examiner—Randall L. Green
Assistant Examiner—G. Gualtieri
Attorney, Agent, or Firm—Peter K. Kontler

[57] ABSTRACT

A catamenial tampon is assembled from a cylindrical pledget of compressible absorbent material, such as rayon or cotton, and a rectangular blank of foraminous sheet material. The central portion of the blank is placed adjacent one end face of the pledget, and the pledget is then pushed axially through a tubular die with its one end face leading so that the annular portion of the blank around the central portion is draped around the entire peripheral surface of the pledget and the converted blank forms a cup with an annular rim extending beyond the other end face of the pledget. The rim is then folded over the other end face of the pledget, and the resulting assembly is provided with a removal cord subsequent to simultaneous reduction of the diameters of the cup and pledget to complete the making of a tampon which is ready for use or for insertion into the tube of an applicator.

7 Claims, 1 Drawing Sheet

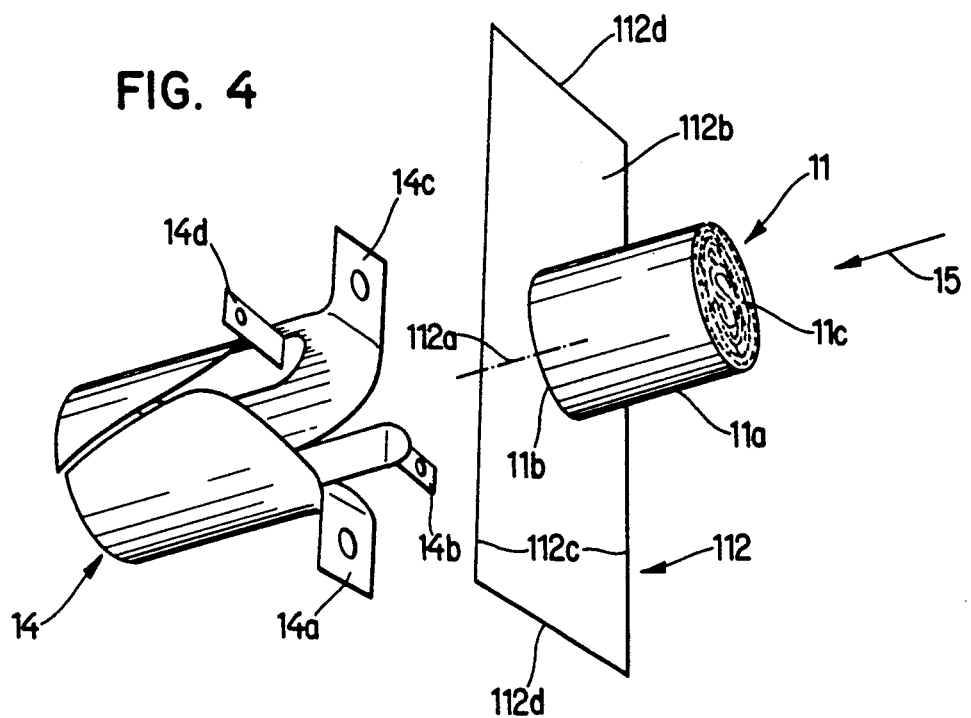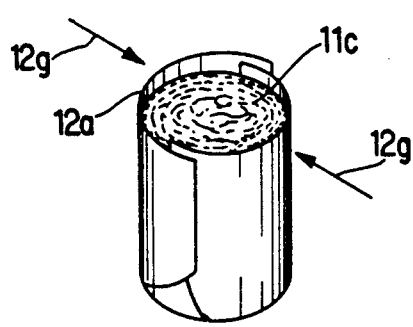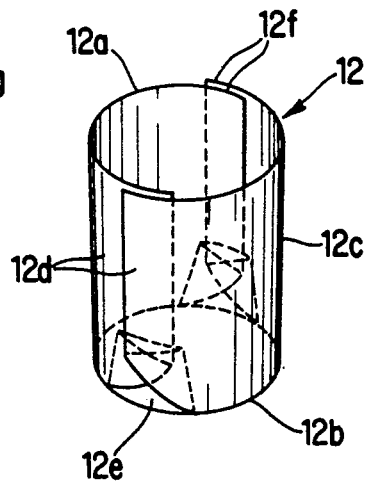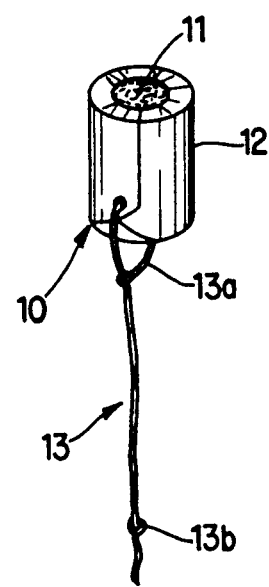

TAMPON

BACKGROUND OF THE INVENTION

The invention relates to tampons in general, especially to digital and applicator type catamenial tampons. More particularly, the invention relates to improvements in tampons of the type wherein a wad or pledget of absorbent material is confined in an envelope of foraminous sheet material (called coverstock).

It is well known to confine a pledget of absorbent material (such as cotton or rayon) in an envelope of foraminous sheet material (hereinafter called coverstock for short) so that the fibers of the pledget are prevented from remaining, or are less likely to remain, in the vagina or in another body cavity which receives the finished tampon, either as a result of digital insertion or with the assistance from an applicator. As a rule, coverstock is supplied by the makers of such products in the form of large rolls which are subdivided into blanks for draping around discrete pledgets of absorbent material. In many instances, pledgets are in the form of cylinders called memory cylinders due to their tendency to expand subsequent to (a) draping into coverstock and (b) compression in directions to reduce their diameters to a fraction of the diameter of an uncompressed and undraped cylinder.

In accordance with a presently known proposal, memory cylinders are draped into square blanks of coverstock. One end face of a cylinder to be draped is placed against the central portion of the square blank, and the remaining portion of the blank is folded or draped against the peripheral surface of the cylinder. This results in conversion of the originally square blank into a cup with a bottom end wall which overlies the one end face of the cylinder and with a cylindrical wall which surrounds a substantial portion of the peripheral surface of the cylinder. The cup has a rim with alternating hills and valleys. The hills have tips which project beyond the other end face of the cylinder, and the deepmost portions of the valleys are located between the two end faces. The tips of the hills can be folded over the other end face of the cylinder in order to ensure that at least a portion of the other end face is also overlapped by the material of the coverstock.

In accordance with another prior proposal, coverstock is converted into a bag which confines the pledget of absorbent material not unlike a tea bag confines a supply of tea leaves. It was also proposed to weld the folds or pleats which develop along the peripheral surface of a memory cylinder in order to enhance the stability of the envelope of coverstock. A drawback of such proposal is that the welded pleats resist expansion of confined absorbent material when the latter is in the process of gathering menses or other body fluids.

OBJECTS OF THE INVENTION

An object of the invention is to provide a tampon wherein the coverstock is applied over a pledget of absorbent material in a novel and improved way so that by far the major part of or the entire pledget is confined within a relatively small coverstock.

Another object of the invention is to provide a tampon wherein the coverstock need not be welded and/or converted into a bag in order to ensure reliable confinement of absorbent material.

A further object of the invention is to provide a novel and improved blank of coverstock which can be converted into an envelope for the absorbent material of the above outlined tampon.

An additional object of the invention is to provide a tampon wherein at least one end face and the entire peripheral surface of a cylindrical or substantially cylindrical pledget are invariably confined in coverstock.

Still another object of the invention is to provide a tampon wherein the quantity of surplus coverstock adjacent the peripheral surface of the cylindrical pledget is a small fraction of surplus coverstock in conventional tampons.

A further object of the invention is to provide a tampon which is safer than heretofore known tampons in that it greatly reduces the likelihood of direct contact between absorbent material and the tissue surrounding a body cavity.

SUMMARY OF THE INVENTION

The invention resides in the provision of a digital or applicator type tampon, particularly a catamenial tampon, which comprises a compressible pledget preferably in the form of a memory cylinder of cotton, rayon or other absorbent material, and a foraminous envelope for the pledget. The envelope completely surrounds the peripheral surface and at least one end face of the cylinder. The envelope comprises or constitutes a cup which confines the pledget and has an annular rim extending beyond and being preferably folded over the other end face of the pledget.

The envelope comprises a bottom end wall which is adjacent the one end face of the pledget and a tubular wall which surrounds the peripheral surface of the pledget and includes a plurality of sections including two substantially semicylindrical shell- or trough-shaped sections with overlapping marginal portions which extend from the one end face at least to but preferably beyond the other end face of the pledget. The sections of the tubular wall preferably further include two additional sections which alternate with the substantially semicylindrical sections and extend from the bottom end wall toward but short of the other end face of the pledget.

In accordance with a desirable and advantageous feature of the invention, the envelope constitutes a converted polygonal blank having a shape other than a square shape, preferably a rectangular shape.

A removal cord or drawstring is connected with the pledget, preferably in the region of the one end face, and extends from the envelope.

The bottom end wall of the aforementioned cup is or can be substantially flat and is at least substantially devoid of wrinkles, pleats and like irregularities. The multi-section tubular wall surrounds the entire peripheral surface of the pledget. Such tubular wall includes at least two sections (particularly the aforementioned substantially semicylindrical sections) which extend beyond the other end face of the pledget and are preferably, or can be, large enough to overlie the entire other end face when folded radially inwardly at the respective axial end of the pledget.

The novel features which are considered as characteristic of the invention are set forth in particular in the appended claims. The improved tampon itself, however, both as to its construction and the mode of making the same, together with additional features and advantages thereof, will be best understood upon perusal of the following detailed description of certain presently preferred specific embodiments with reference to the accompanying drawing.

BRIEF DESCRIPTION OF THE DRAWING

FIG. 1 is a perspective view of an assembled tampon as it appears prior to simultaneous reduction of the diameters of the envelope and the pledget;

FIG. 2 is an enlarged perspective view of the envelope as it appears prior to folding of the rim;

FIG. 3 is an enlarged perspective view of the pledget and of the envelope prior to application of the removal cord; and FIG. 4 is an exploded perspective view showing a substantially cylindrical pledget at one side, and a tubular folding die at the other side, of a rectangular blank of foraminous sheet material.

DESCRIPTION OF PREFERRED EMBODIMENTS

FIG. 1 shows an assembled tampon 10 as it appears prior to a reduction of its diameter to standard size. The tampon 10 comprises a substantially cylindrical pledget 11 in the form of a so-called memory cylinder which is made of cotton, rayon and/or other suitable absorbent material. The pledget 11 is confined in a cup-shaped envelope 12 having an annular rim 12a (FIGS. 2 and 3) which extends beyond the respective end face (11c) of the pledget. The lower end face 11b of the pledget 11 (as seen in FIGS. 1 and 3) is adjacent the circular disc-shaped bottom end wall 12b of the envelope 12, and the cylindrical peripheral surface 11a (FIG. 4) of the pledget is completely surrounded by a multi-section tubular wall 12c of the envelope. The tampon 10 further comprises a removal cord or drawstring 13 which has a looped end portion 13a anchored in the pledget 11 adjacent the end face 11b and extends through and from the tubular wall 12c of the envelope 12. The removal cord 13 is provided with a knot 13b, e.g., in a manner as disclosed in commonly owned U.S. Pat. No. 4,836,587 granted June 6, 1989 to Alfred Hinzmann.

The tubular wall 12c of the envelope 12 comprises two substantially semicylindrical shell- or trough-shaped main sections 12d with marginal portions 12f overlapping each other and extending in parallelism with the common axis of the pledget 11 and envelope 12 from the bottom end wall 12b toward and beyond the end face 11c to form the annular rim 12a. The tubular wall 12c further comprises two additional substantially concavo-convex sections 12e (one shown in FIG. 2) which alternate with the sections 12d and extend from the bottom end wall 12b toward but short of the end face 11c of the pledget 11.

When the conversion of a polygonal (preferably rectangular) blank 112 (FIG. 4) of foraminous sheet material (coverstock) into the envelope 12 is completed, the annular rim 12a is folded over the end face 11c of the pledget 11 in directions indicated in FIG. 3 by arrows 12g so that the resulting converted cup fully confines the end face 11b, the entire peripheral surface 11a and at least a portion, but preferably at least the major part, of the end face 11c of the pledget 11, i.e., the latter is substantially completely confined in the envelope 12 so that its fibers cannot come in contact with the skin or tissue surrounding the body cavity into which the finished tampon is inserted, either digitally or by means of a standard applicator.

The dimensions of the blank 112 are selected in such a way that the envelope 12 which is obtained upon conversion of this blank into a cup completely confines the end face 11b and the peripheral surface 11a of the pledget and preferably extends beyond the end face 11c so that its rim 12a can be folded over in the directions which are indicated by arrows 12g. It is preferred to employ a rectangular blank 112 wherein the length of each of the two longer sides 112c is at least 1.5 times the length of either of the two shorter sides 112d. The sides 112c and 112d surround an annular (remaining or second) portion of the blank 112 which, in turn, surrounds a circular disc-shaped central portion 112a.

FIG. 4 further shows a tubular folding die 14 which is used to cooperate with the pledget 11 in order to convert the blank 112 into an envelope 12. This die is assembled of four parts 14a, 14b, 14c, 14d defining a tunnel or channel for the passage of the pledget 11. The inlet of the channel preferably resembles a conical frustum to facilitate penetration of the pledget 11 into the die 14. The pledget does not directly contact the parts 14a to 14d of the die 14 because it preferably serves as a means for pushing (with its end face 11b) the central portion 112a of the blank 112 into the channel so that the central portion 112a penetrates into and advances in and beyond the channel whereby the second or remaining portion 112b of the blank 112 is automatically draped around the peripheral surface 11a to form the tubular wall 12c with its rim 12a. The manner in which the rim 12a is thereupon folded over the end face 11c of the pledget 11 in the envelope 12 by suitable folding arms of in any other way is not shown in the drawing; such folding takes place in directions which are indicated by the aforementioned arrows 12g and is normally carried out simultaneously with a reduction of the diameter of the envelope 12. The attachment of removal cord 13 normally follows compression of the envelope 12 and pledget 11.

The blank 112 is preferably severed from the leader of an elongated web or strip of foraminous sheet material (coverstock) which is drawn from a large bobbin or reel of the type customarily employed for the making of coverstocks which surround the pledgets of catamenial tampons. It is preferred to maintain the blank 112 in a substantially vertical plane when its central portion 112a is adjacent the inlet of the channel or tunnel in the tubular die 14 and the other side of the central portion 112a is positioned adjacent the end face 11b of the pledget 11. The latter is then advanced in the direction of arrow 15 (e.g., by a plunger or the like, not shown) to push the blank 112 into the die 14 and to thus convert the blank into an envelope 12.

The operation which is carried out to convert the blank 112 into an envelope 12 surrounding the pledget 11 is performed by an automatic machine which is preferably designed to turn out large numbers of tampons per unit of time and which is further equipped with automatic means for compressing or compacting the tampons in order to reduce the diameters of the envelopes and of the respective pledgets and to simultaneously fold the rims 12a, and for thereafter applying removal cords 13. The compressing or compacting step can take place simultaneously with, or can precede or follow, a step of forming the tampon with a rounded head in the region of the end face 11c of the pledget in order to facilitate insertion of the finished product into a body cavity.

By way of example, each blank 112 can be 130 mm long and 60 mm wide, i.e., the length of each blank can be a multiple of its width. Such blanks can be converted into envelopes 12 of the type shown in FIGS. 1 to 3. A blank 112 having the just outlined dimensions can confine a pledget much more satisfactorily than a square blank which is 95 mm wide and 95 mm long even though the area (7800 mm²) of the rectangular blank is much smaller than the area (9025 mm²) of a square blank. Savings in the material (coverstock) of blanks amount to 14 percent.

Another important advantage of the improved tampon is that the tampon can be made in existing coverstock modules of tampon making machines; all that is necessary is to subdivide a web of coverstock into differently dimensioned and/or configurated blanks and to employ the die 14 or an equivalent tool.

The means for making applicators for the improved tampons is or can be the same as disclosed in commonly owned U.S. Pat. No. 4,755,164 granted July 5, 1988 to Alfred Hinzmann and in patents which are referred to therein.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A tampon comprising a compressible substantially cylindrical pledget of absorbent material, said pledget having a peripheral surface and two end faces; and a foraminous envelope for the pledget, said envelope completely surrounding said peripheral surface and at least one end face of the pledget and comprising a bottom end wall adjacent said at least one end face and a tubular wall surrounding said peripheral surface and comprising a plurality of sections including two substantially semicylindrical sections having overlapping marginal portions extending from said at least one end face at least to the other of said end faces.

2. The tampon of claim 1, wherein said envelope comprises a cup which confines said pledget and includes an annular rim extending beyond the other of said end faces.

3. The tampon of claim 1, wherein said sections further include two additional sections alternating with said substantially semicylindrical sections and extending from said bottom end wall toward but short of the other end face of said pledget.

4. The tampon of claim 1, wherein said envelope consists of a folded rectangular blank of foraminous sheet material.

5. The tampon of claim 1, further comprising a removal cord connected with aid pledget and extending from said envelope.

6. A tampon comprising a compressible substantially cylindrical pledget of absorbent material, said pledget having a peripheral surface and two end faces; and a foraminous envelope for the pledget, said envelope completely surrounding said peripheral surface and at least one end face of said pledget and including a cup having a flat bottom end wall which is substantially devoid of wrinkles and overlies said at least one end face, said cup further having a multi-section tubular wall surrounding the peripheral surface of said pledget and including a plurality of overlapping concavo-convex sections with at least two of said sections extending beyond the other of said end faces.

7. The tampon of claim 6, wherein said at least two sections overlie the other end face of said pledget.

* * * * *